(12) United States Patent
Novak

(10) Patent No.: US 7,115,121 B2
(45) Date of Patent: Oct. 3, 2006

(54) ELECTROSURGICAL APPARATUS

(75) Inventor: Pavel Novak, Stetten (CH)

(73) Assignee: Storz Endoskop GmbH, (CH)

( * ) Notice: Subject to any disclaimer, the term of this patent is extended or adjusted under 35 U.S.C. 154(b) by 355 days.

(21) Appl. No.: 10/730,585

(22) Filed: Dec. 8, 2003

(65) Prior Publication Data

US 2004/0172015 A1   Sep. 2, 2004

Related U.S. Application Data

(63) Continuation of application No. PCT/EP02/05806, filed on May 27, 2002.

(30) Foreign Application Priority Data

Jun. 8, 2001 (DE) ................................ 101 28 377

(51) Int. Cl.
*A61B 18/18* (2006.01)

(52) U.S. Cl. ............................. 606/37; 606/34; 606/39; 606/40

(58) Field of Classification Search ............ 606/32–34, 606/38–41, 45–50
See application file for complete search history.

(56) References Cited

U.S. PATENT DOCUMENTS

| | | | | |
|---|---|---|---|---|
| 4,154,240 A | * | 5/1979 | Ikuno et al. | .................... 606/37 |
| 4,188,927 A | * | 2/1980 | Harris | .......................... 606/38 |
| 4,398,534 A | * | 8/1983 | Hagiwara | ..................... 606/37 |
| 4,463,759 A | * | 8/1984 | Garito et al. | .................. 606/42 |
| 4,827,927 A | * | 5/1989 | Newton | ......................... 606/37 |
| 6,197,024 B1 | * | 3/2001 | Sullivan | ....................... 606/45 |
| 6,652,514 B1 | * | 11/2003 | Ellman et al. | ................. 606/37 |

FOREIGN PATENT DOCUMENTS

| | | |
|---|---|---|
| DE | 24 29 021 | 1/1976 |
| DE | 24 57 221 | 6/1976 |
| DE | 30 45 996 | 7/1982 |
| DE | 36 00 990 | 7/1987 |
| DE | 101 28 377 | 1/2003 |
| EP | 0 186 369 | 7/1986 |

* cited by examiner

*Primary Examiner*—Michael Peffley
(74) *Attorney, Agent, or Firm*—St. Onge Steward Johnston & Reens, LLC

(57) ABSTRACT

An electrosurgical apparatus comprises an HF generator and an HF instrument, the HF instrument having a first switch and a second switch, the first switch being assigned a first operating state, and the second switch being assigned a second operating state of the HF generator, the first switch and the second switch further being connected to at least one control signal line, there being assigned, furthermore, to the first switch and the second switch signal coding means that, as a function of the switching state of the first and the second switch, generate from a control input signal different control output signals for the optional activation of the first operating state or of the second operating state of the HF generator, which are fed to the HF generator via the common control line, and the HF instrument furthermore having at least a third switch, which is assigned at least a third operating state of the HF generator. The third switch is connected to the at least one control signal line in such a way that, upon actuation of the third switch, a further control output signal is generated for the activation of the third operating state and is fed to the HF generator via the at least one control signal line.

10 Claims, 3 Drawing Sheets

ELECTROSURGICAL APPARATUS

CROSS-REFERENCE TO PENDING APPLICATION

The present invention is a continuation of pending International Patent Application PCT/EP 02/05806 filed on May 27, 2002 which designates the United States and claims priority of German patent application 101 28 377.6 filed on Jun. 8, 2001.

BACKGROUND OF THE INVENTION

The invention relates to an electrosurgical apparatus, comprising an HF generator and an HF instrument.

An apparatus of the type mentioned at the beginning is used in what is termed electrosurgery. High-frequency currents generated by the HF generator are led into the body of a patient via the HF instrument connected to the HF generator, particularly in the course of minimally invasive surgery, in order to use the HF instrument at an operating site to coagulate and/or to cut tissue under the action of the high-frequency currents. During the coagulation, vessels are obliterated in order to cause hemostatis upon removal of tissue. The coagulation and the cutting by means of high-frequency current differ from one another with regard to the applied power of the high-frequency current and, if appropriate, with regard to the duration of the application. In the coagulation mode of an electrosurgical apparatus, work is performed as a rule with relatively low HF powers and intermittently, whereas higher HF powers are required to cut tissue by means of high-frequency current, in order to generate the electric arc required for cutting tissue by means of high-frequency current. Furthermore, work is also not performed intermittently during cutting, but continuously.

In accordance with these two previously described operating modes of coagulation and cutting, the HF generator of such an electrosurgical apparatus is capable of providing high-frequency currents with the corresponding powers required for coagulation and cutting.

When working with an HF instrument, however, the operating modes of "coagulation" and "cutting" are, as a rule, not required simultaneously, but alternately, that is to say the work steps of cutting and coagulation take place one after another and alternately, but not simultaneously. The HF generator can be activated correspondingly with the aid of the operating modes of "coagulation" and "cutting".

So that the surgeon operating the HF instrument need not undertake the activation of the operating modes at the HF generator situated away from the operating table and in the non-sterile area of the operating room, or need not appropriately instruct an assistant to switch over between the operating modes, the HF instrument itself is provided with a possibility for activating the operating modes in the form of two switches that can be operated with the fingers.

For example, the first switch is assigned the operating mode of "coagulation" and the second switch is assigned the operating mode of "cutting". Consequently, there correspond in each case to the first switch and the second switch a first operating state, for example a relatively high output power of the HF generator, or a second operating state, for example lower output power with a possibly intermittent operation.

The first switch and the second switch are connected to at least one control signal line, which is connected to the main line of the HF instrument via which the active electrode at the distal end of the HF instrument is fed. In addition to the high-frequency current, the main line feeds in a control input signal from which, depending on which of the two switches is actuated, a corresponding control output signal for activating the operating state assigned to the actuated switch is generated with the aid of the signal coding means, which control output signal is fed to the HF generator via that control signal line to which the respective switch is connected, in order to activate the corresponding operating state of the HF generator.

In an apparatus disclosed in DE 30 45 996 A1, in addition to the previously mentioned two switches for switching over between the operating modes of "coagulation" and "cutting", still further switches are provided on the HF instrument, specifically for respectively increasing or lowering the output power in the operating mode respectively selected. Additional signal lines are required in the case of this known apparatus in order to implement the further functions for switching over the HF generator.

An apparatus comparable thereto is disclosed in EP 0 186 369 A1 and likewise has four switches for switching over between the operating modes of "coagulation" and "cutting", as well as for increasing or lowering the output power in each of the two operating modes. Three signal lines are required overall for the four switches in the case of this known apparatus.

SUMMARY OF THE INVENTION

It is therefore an object of the invention to develop an electrosurgical apparatus of the type mentioned at the beginning so as to create with the least possible outlay on construction an activation possibility of the first, second and at least one third operating state of the HF generator from the location of the HF instrument, in particular so that no additional control signal lines are required for the at least one third switching function.

According to a first aspect of the invention, an electrosurgical apparatus is provided, comprising an HF generator having a first operating state, a second operating state and at least one third operating state; an HF instrument having a first switch assigned to said first operating state, a second switch assigned to said second operating state, and at least one third switch assigned to said at least one third operating state; at least one control signal line, said first, second and at least one third switches being connected to said HF generator via said at least one control signal line, said first, second and at least one third switches generate a first, a second or at least one third control output signal which differ from one another, from a control input signal as a function of a switching state of said first, second and said at least one third switches, in order to optionally actuate one of said first, second and at least one third operating states of said HF generator, said first, second and at least one third control output signals being fed to said HF generator via said at least one control signal line only.

According to a second aspect of the invention, an electrosurgical apparatus is provided, comprising an HF generator having a first operating state, a second operating state and at least one third operating state; an HF instrument having a first switch assigned to said first operating state, a second switch assigned to said second operating state, and at least one third switch assigned to said at least one third operating state; at least one control signal line, said first, second and at least one third switches being connected to said HF generator via said at least one control signal line; a first signal coder assigned to said first switch, a second signal coder assigned to said second switch, wherein said first signal coder and said second signal coder are also assigned to said at least one third switch; said first, second and at least one third switches generate a first, a second or at least one third control output signal which differ from one another, from a control input signal as a function of a switching state of said first, second and said at least one third switches, in order to optionally activate one of said first, second and at least one third operating states of said HF generator, said first, second and at least one third control output signals being fed to said HF generator via said at least one control signal line only.

According to a third aspect of the invention, an electrosurgical apparatus is provided, comprising an HF generator having a first operating state, a second operating state and at least one third operating state; an HF instrument having a first switch assigned to said first operating state, a second switch assigned to said second operating state, and at least one third switch assigned to said at least one third operating state; at least one control signal line, said first, second and at least one third switches being connected to said HF generator via said at least one control signal line; a first signal coder assigned to said first switch, a second signal coder assigned to said second switch, a third signal coder assigned to said at least one third switch is differing from said first and second signal coder; said first, second and at least one third switches generate a first, a second or at least one third control output signal which differ from one another, from a control input signal as a function of a switching state of said first, second and said at least one third switches, in order to optionally actuate one of said first, second and at least one third operating states of said HF generator, said first, second and at least one third control output signals being fed to said HF generator via said at least one control signal line only.

Instead of providing additional control signal lines in the HF instrument in the case of more than two switches being provided, in the case of the apparatus according to the invention, the outlay on construction is advantageously kept low when implementing the switchover to a third operating mode of the HF generator by virtue of the fact that the third switch is also connected to the respectively present, for example common, control signal line, thus saving additional control signal lines. The signal coding means for generating the control output signals are preferably designed such that upon actuation of the third switch from the control input signal, which is preferably the same for all three switches, an additional control output signal is generated that differs from the control output signals for activating the first and second operating states, in order to activate the third operating state of the HF generator. According to the invention, this further control output signal is fed to the HF generator via the common control signal line.

In a preferred refinement, the third switch connects a main line that is connected to the HF generator directly to the control signal line.

This measure has the advantage that a structurally very simple circuit without an additional control signal line is implemented and can be used to activate the third operating state of the HF generator. The previously mentioned main line, which is connected to the HF generator, also serves in this case as a feed for the control signal. If this control signal consists, for example, of an alternating current, upon actuation of the third switch, this alternating current is fed again unchanged to the HF generator via the control signal line, while upon actuation of the first or second switch via the corresponding signal coding means a change is caused in this alternating current signal in order to activate the first or second operating state correspondingly.

In a preferred refinement, the signal coding means assigned to the first and second switches are also assigned to the third switch.

This measure has the advantage that, for the at least one third switching function, not only is use made of the control signal lines already present, so that no additional control signal line is required, but also that use is made of the already present signal coding means and no additional signal coding means are required, the result being to reduce the structural outlay even further.

In a preferred refinement, the third switch is connected to the first switch and the second switch in such a way that its closed state corresponds to a simultaneous closed state of the first and second switches.

This measure leads to a particularly simple integration of the third switch in the system composed of first and second switches, the further advantage consisting in that it is possible to make use as signal coding means for generating the control output signals of the same signal coding means as for an apparatus having only two switches, as previously described. However, instead of now having to actuate the first switch and the second switch jointly, this measure has the further advantage of simple operation, since only one switch need be actuated, specifically the third one, in order to produce this switching state.

In a further preferred refinement, the third switch is connected electrically in parallel with the first and second switches, which can be implemented by only a few additional lines and thus in a structurally simple way.

As an alternative to this, it is also preferred in a second refinement if the third switch is coupled mechanically to the first and second switches in such a way that, upon actuation of the third switch, the first and the second switches are simultaneously closed.

This measure has the advantage that the outlay on circuitry by comparison with the system with two switches is not increased at all by the third switch, because the third switch is coupled to the first and the second switches only mechanically. The mechanical coupling of the third switch to the first and second switches must, of course, fulfill the condition that it must be possible to actuate the first and the second switches independently of one another despite the mechanical coupling to the third switch in order, in addition to the third operating state, also to be able activate the first and second operating states of the HF generator independently of one another.

In a particularly preferred refinement, the signal coding means have a first diode, assigned to the first switch, and a second diode, assigned to the second switch, the first and second diodes being connected to the control signal line with reversed polarity.

This refinement of the signal coding means, which is already known in the case of apparatuses capable of switching over between two operating modes is particularly advantageous within the scope of the present invention because these two diodes connected with mutually reversed polarity and in parallel with one another suffice to activate the third operating mode via the third switch by virtue of the fact that actuating the third switch enables the flow of current through both diodes simultaneously. While the first diode passes the positive half wave of the input signal, for example, and thus activates the first operating state, and the second diode passes the negative half wave upon actuation of the second switch in order to activate the second operating state, upon actuation of the third switch the full input signal is fed again to the HF generator in order to activate the third operating state. Consequently, there is no need for a specific signal detection in the case of the HF generator.

As an alternative to the previously mentioned refinement in accordance with which the signal coding means assigned to the first and second switches are also assigned to the third switch, it is likewise preferred in an alternative refinement for a dedicated signal coding means to be assigned to the third switch.

This measure has the advantage, particularly in conjunction with the refinement, that the at least one third switching function constitutes a combination of the first and second switching functions because a better "simultaneity" of the actuation of the at least one third switching function is achieved than when the first and second switching functions are coupled to one another mechanically in order to implement the third switching function.

It is preferred moreover in this case when the signal coding means assigned to the third switch correspond to a parallel connection of the signal coding means assigned to the first and second switches.

Again as in the case of one of the previously mentioned refinements, this measure enables a third switching function that leads to an operating state of the HF generator which corresponds to a combination of the first and second operating states of the HF generator, particularly when the signal coding means have corresponding diodes.

In the case of this refinement, it is possible, for example, without a specific signal detection to implement in addition to the operating modes of "coagulation" and "cutting" as third operating mode a fast, alternating activation of the output power for cutting and of the output power for coagulation, as is useful in arthroscopy. Other operating states can, however, likewise be taken into consideration.

In a further, likewise preferred alternative refinement, the signal coding means assigned to the third switch have other coding properties than the signal coding means assigned to the first and/or second switches.

The advantage is thereby achieved that it is possible without an additional control line to achieve an additional coding that does not, as previously, correspond to alternation of the first and second operating states but rather it is possible to set a completely different third operating state. This refinement is also suitable for even further switches, for example a fourth or fifth switch. It is preferred in this case when the signal coding means assigned to the third switch and/or the signal coding means assigned to the first and/or second switches have at least one Zener diode in order to implement the at least one third operating state in a way independent of the first and/or second operating states. A change in or limitation of voltage of the control signal, for example, can be produced with the aid of such a Zener diode.

Furthermore features and advantages emerge from the following description and the attached drawing.

It goes without saying that the abovementioned features, and those still to be explained below can be used not only in the respectively specified combination, but also in other combinations or on their own without departing from the scope of the present invention.

BRIEF DESCRIPTION OF THE DRAWINGS

Exemplary embodiments of the invention are illustrated in the drawing and will be described in more detail hereinafter with reference to the drawing, in which.

DETAILED DESCRIPTION OF PREFERRED EMBODIMENTS

Figure 1:
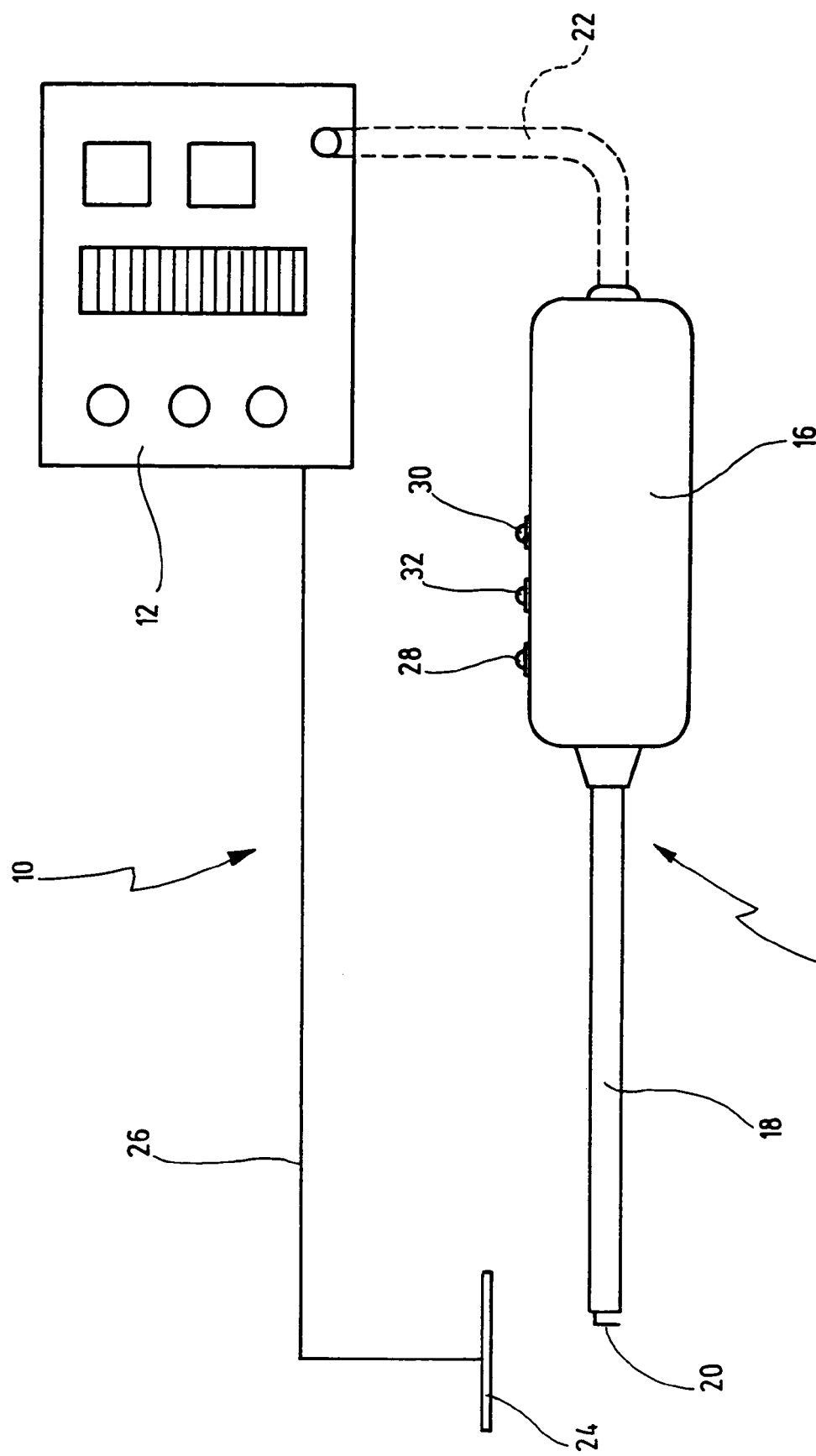
FIG. 1 shows a schematic overall illustration of an electrosurgical apparatus that enables three operating modes.

FIG. 1 illustrates schematically an electrosurgical apparatus provided with the general reference numeral 10. The apparatus 10 is used in the field of HF surgery.

The apparatus 10 has an HF generator 12 that generates high-frequency currents and/or voltages of a few hundred kHz. The HF generator 12 is capable of generating high-frequency currents with an output power that is suitable for the coagulation of tissue, and of generating high-frequency currents with an output power that is suitable for the cutting of tissue.

The apparatus 10 further has an HF instrument 14 with the aid of which the high-frequency currents generated by the HF generator 12 can be applied in the human or animal body to the tissue to be treated.

At its proximal end, the HF instrument 14 has a handpiece 16 and a shank 18 that is connected to the handpiece 16 and is of elongated design with a small diameter such that it is suitable for minimally invasive surgery.

Arranged at the distal end of the shank 18 is an electrode 20 to which, as active electrode, it is possible to apply the high-frequency current of the HF generator 12. The HF generator 12 is connected for this purpose to the handpiece 16 of the HF instrument 14 via an appropriate cable 22, and the high-frequency current of the HF generator is conducted via an appropriate supply lead (not illustrated) to the active electrode 20 through the handpiece 16 and through the shank 18.

Moreover, a neutral electrode 24 is connected to the HF generator 12 via a line 26, the neutral electrode 24 usually being connected to the surface of the patient's body in order to close the HF circuit via the surface of the patient's body. The arrangement illustrated in FIG. 1 is therefore a monopolar HF arrangement, the present invention not, however, being limited to such a monopolar application, but also being suitable for bipolar applications. In bipolar applications, the neutral electrode is arranged in immediate vicinity of the active electrode 20 on the HF instrument itself.

Arranged on the handpiece 16 is a first switch 28 in the form of a first key 28, a second switch 30 in the form of a second key and a third switch 32 in the form of a third key.

The three switches 28, 30 and 32 serve the purpose of activating a specific operating state of the HF generator upon their optional actuation.

It is provided without limitation of generality in the case of the exemplary embodiment illustrated in FIG. 1 that, upon actuation of the first switch 28, an operating state of the HF generator 12 is activated that corresponds to the operating mode of "coagulation", that is to say the HF generator 12 generates a high-frequency current of lower output power and is, if appropriate, temporally interrupted. Upon actuation of the second switch 30, a second operating state of the HF generator 12 is activated that corresponds to the operating mode of "cutting", that is to say in this operating state the HF generator generates a high-frequency current with an output power that is higher in relation to the first operating state, and without temporal interruption. Upon actuation of the third switch 32, a third operating state of the HF generator 12 is activated that corresponds to a third operating mode of "fast, alternating activation of the cutting and coagulation current", that is to say in this operating state the HF generator alternately generates high-frequency currents that are suitable for coagulation or for cutting.

The switches 28, 30 and 32 are preferably designed in the form of keys, that is to say activation of the appropriate operating state is performed in each case as long as the appropriate key is kept pressed.

Figure 2:
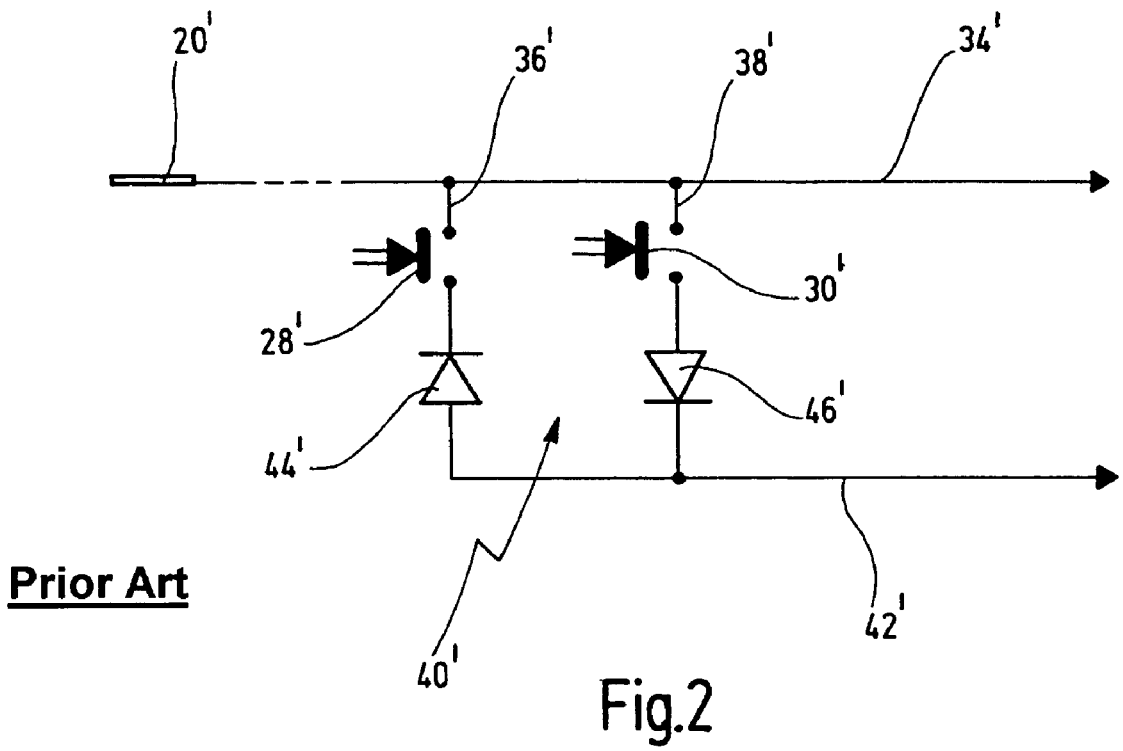
FIG. 2 shows a sketched circuit diagram of a known apparatus with two switches for switching over between two operating modes.
Figure 3:
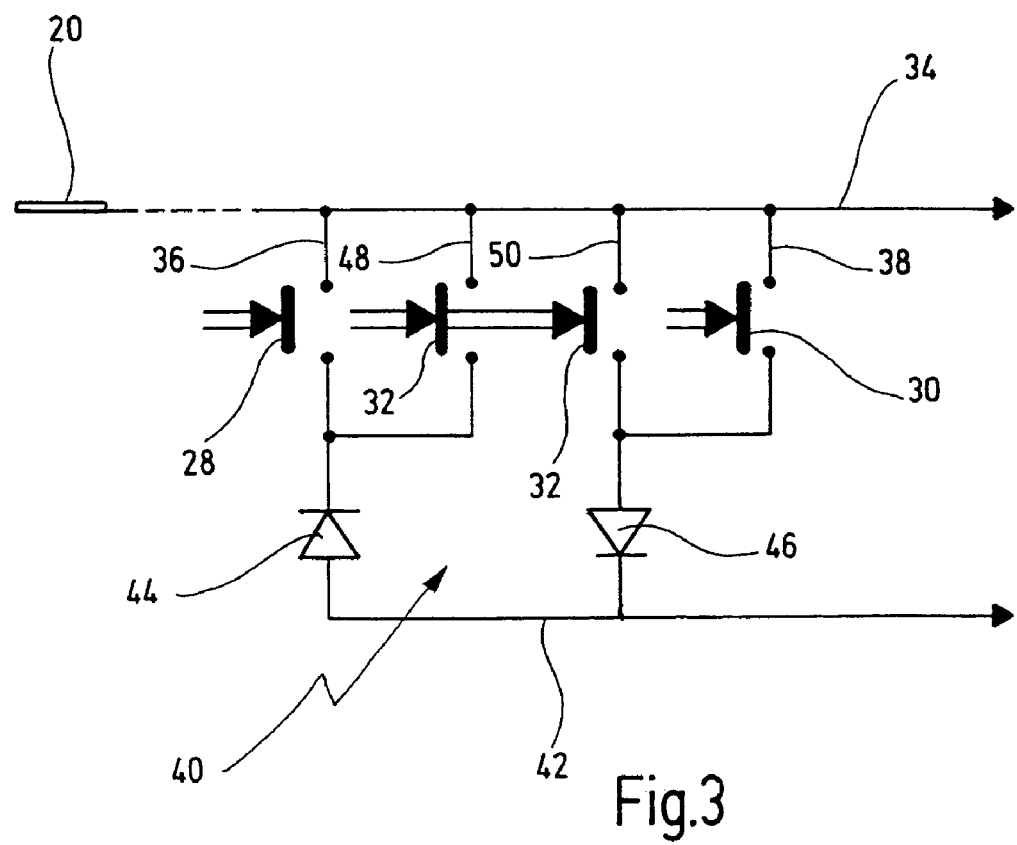
FIG. 3 shows a sketched circuit diagram of the apparatus in FIG. 1, in the case of which, in accordance with the present invention, the apparatus in FIG. 2 with two switches has been expanded to three switches.

With reference to FIGS. 2 and 3, a more detailed description of the activation of the operating states of the HF generator 12 now follows with the aid of two circuit diagrams.

Shown firstly in FIG. 2 is a sketched circuit diagram of an HF instrument that is known from the prior art and has only two switches 28' and 30' for switching over between the operating modes of "coagulation" and "cutting". Components comparable to the HF instrument 14 in FIG. 1 have been provided with the same reference numerals, supplemented by a prime. The electrode 20' is connected to the HF generator via a main line 34' that extends through the shank and the handpiece of the HF instrument.

Departing from the main line 34' are branch lines 36' and 38' via which the switches 28' and 30' are connected to the main line 34'.

The switches 28' and 30' are assigned signal coding means 40'.

Furthermore, via the branch lines 36' and 38', the switches 28' and 30' are connected to a control signal line 42' that is common in the preferred exemplary embodiment shown and is connected in turn to the HF generator 12'.

In addition to the high-frequency current that is applied to the electrode 20', there is fed in via the main line 34' a control input signal from which, as a function of the switching state of the first switch 28' or of the second switch 30', the signal coding means 40' generate a corresponding control signal that is fed back again via the control signal line 42' into the HF generator 12' in order to activate the operating state that is assigned to the corresponding switch 28' or 30'.

The signal coding means 40' have a first diode 44' and a second diode 46' that are connected to the control signal line 42' with mutually reversed polarity.

The mode of operation of the circuit illustrated in FIG. 2 will now be described in more detail. In addition to the high-frequency alternating current, a preferably low-frequency alternating current that is applied to the electrode 20' is additionally fed into the main line 34' as control input signal.

If the first switch 28' is now actuated, that is to say closed, the circuit for this alternating current additionally fed in is closed via the branch line 36', the first switch 28', the first diode 44' and the control signal line 42'. The first diode 44' in this case respectively passes only the positive half wave of the alternating current. The positive half wave of the alternating current additionally fed in now serves as control output signal that is fed via the control signal line 42' to the HF generator 12' in order to activate the first operating state, that is to say in order to activate the operating mode of "coagulation".

If, instead of the first switch 28', the second switch 30' is actuated, that is to say closed, the circuit for the alternating current additionally fed in is closed via the branch line 38', the second switch 30', the second diode 46' and the common control signal line 42'. By contrast with the diode 44', the second diode 46' passes only the negative half wave of the alternating current additionally fed in, this negative half wave now being fed as control output signal to the HF generator 12' via the common control signal line 42', the second operating state of the HF generator 14' thereby correspondingly being activated. The operating mode of "cutting" is now thereby activated.

The corresponding sketched circuit diagram for the apparatus according to the invention in FIG. 1 is now illustrated in FIG. 3, in which all the circuit elements from FIG. 2 are to be found again, thereby rendering plain the simplicity of the present invention in design terms.

To be precise, the third switch 32 is likewise connected to the control signal line 42 without requiring a further control signal line. The signal coding means 40 are designed such that, upon actuation of the third switch 32, that is to say when the third switch 32 is closed, a further control output signal is generated for activating the third operating state of the HF generator 12, this generated control output signal being fed to the HF generator 12 via the control signal line 42 common to the switches 28 and 30.

In the exemplary embodiment shown, this is implemented by virtue of the fact that the third switch 32 is connected to the first switch 28 and the second switch 30 in such a way that its closed state corresponds to a simultaneous closed state of the first switch 28 and of the second switch 30. For this purpose, the third switch 32 is connected via two further branch lines 48 and 50 to the main line 34, on the one hand, and to the branch lines 36 and 38 of the first switch 28 and the second switch 30, respectively on the other hand.

Upon closure of the third switch 32, the circuit is now closed both via the first diode 44 and via the second diode 46, as a result of which the alternating current additionally fed into the main line 34 is fed again without change to the HF generator 12 via the common signal line 42, thereby activating the third operating state of the HF generator 12, which consists in the present exemplary embodiment in that there is an alternating switching to and fro between the operating modes of "coagulation" and "cutting". Consequently, the third switch 32, and thus the third operating state, neither require an additional control signal line nor an additional control input signal fed into the main line 34, nor does the HF generator 12 require an additional signal detection. The quickly alternating activation of the cutting and coagulation current upon actuation of the third switch 32 is performed, specifically, at the frequency of the alternating current additionally fed in as control input signal when the third switch 32 is closed and, consequently, the positive and the negative half waves of the alternating current additionally fed in is fed again to the HF generator 12 via the control signal line 42.

The frequency of the alternating current fed in can advantageously be preset in this case at the HF generator.

As emerges from FIG. 3, the third switch 32 is connected in parallel with the first switch 28 and in parallel with the second switch 30.

Instead of a parallel electric connection of the third switch 32 with the switches 28 and 30, the same action can be achieved within the scope of the present invention by mechanically coupling the third switch 32 to the first and the second switches 28 and 30 in such a way that, upon actuation of the third switch 32, the first and the second switches 28 and 30 are simultaneously closed. However, in this case the mechanical coupling must be configured in such a way that the first switch 28 and the second switch 30 can also continue to be actuated independently of one another in order to be able to activate the first operating state and the second operating state optionally.

Figure 4:
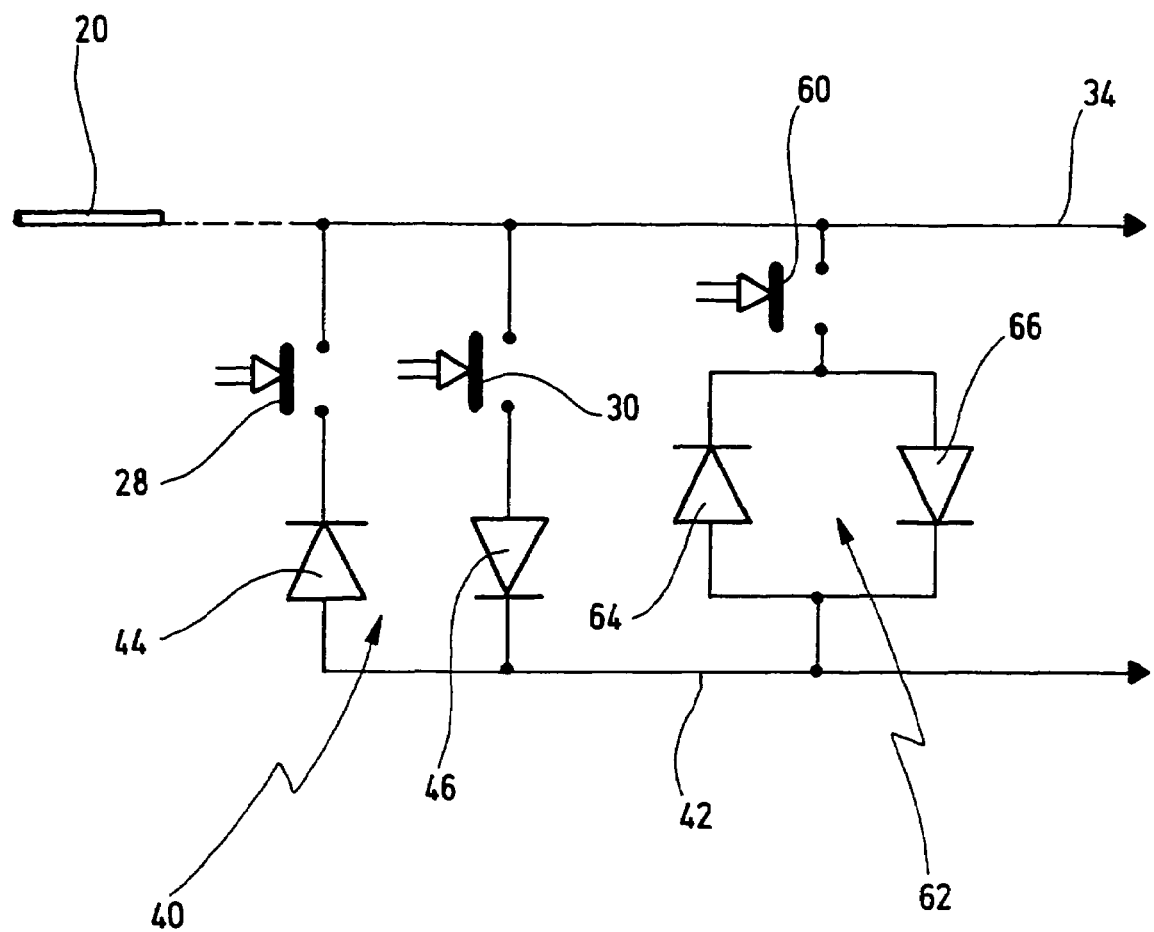
FIG. 4 shows a sketched circuit diagram of a further exemplary embodiment for use in the apparatus in FIG. 1.

A further exemplary embodiment of a circuit with at least one third switch 60 is illustrated in FIG. 4. Parts identical to those in FIG. 3 have been provided with the same reference numerals.

Instead of the third switch 60 being assigned the same signal coding means 40 as the first switch 28 and the second switch 30, the third switch 60 is assigned dedicated signal coding means 62. The signal coding means 62 have a parallel circuit composed of a first diode 64 and a second diode 66 that are connected in parallel with mutually reversed polarity. The diode 64 corresponds in this case to the diode 44, and the diode 66 corresponds to the diode 46.

Upon closure of the switch 60, the flow of current coming from the main line 34 goes simultaneously via the diodes 64 and 66, as a result of which the same switching state is achieved as when the switch 32 is closed in the case of the circuit according to FIG. 3. However, a better "simultaneity" is achieved, if appropriate, with the circuit in accordance with FIG. 4, since only the switch 60 is closed mechanically, being correspondingly not designed as a double switch.

The third operating state of the HF generator 12 implemented by the third switch 60 is the same one as is also set up upon closure of the switch 32.

Instead, as previously described, of assigning the third switch a first diode 64 and a second diode 66 that correspond to the diodes 44 and 46 that are assigned to the first switch 28 and the second switch 30, the diodes 64 and 66 can also be replaced by diodes such as have other coding properties by comparison with the diodes 44 and 46. For example, as is provided in a preferred refinement, it would be possible for the diodes 64 and 66 that effect a voltage limitation of the control signal to be replaced by at least one Zener diode. A completely new, third operating state can thereby be activated at the HF generator.

Otherwise, it would also be possible, conversely, to replace the diodes 44 and 46 by Zener diodes.

Furthermore, it is possible in a further alternative refinement to connect the third switch directly to the main line 34 and the control signal line 42, that is to say to omit the signal coding means 62 completely. In the case of such a circuit, upon closure of the third switch 60, the control signal, for example an alternating current signal, is passed both with a positive and with a negative half wave, and this, in turn, would correspond to the simultaneous closure of the first switch 28 and the second switch 30. An appropriate resistor is provided in the HF generator 12 such that the main line 34 can be directly "short-circuited" with the control signal line 42.

What is claimed is:

1. An electrosurgical apparatus, comprising:
   an HF generator having a first operating state, a second operating state and at least one third operating state;
   an HF instrument having a first switch assigned to said first operating state, a second switch assigned to said second operating state, and at least one third switch assigned to said at least one third operating state;
   a control signal line, said first, second and at least one third switches being connected to said HF generator via said control signal line;
   a first signal coder assigned to said first switch, a second signal coder assigned to said second switch, wherein said first signal coder and said second signal coder are also assigned to said at least one third switch;
   said first, second and at least one third switches generate a first, a second or at least one third control output signal which differ from one another, from a control input signal as a function of a switching state of said first, second and said at least one third switches, in order to optionally activate one of said first, second and at least one third operating states of said HF generator, said first, second and at least one third control output signals being fed to said HF generator via said control signal line only.

2. The apparatus of claim 1, wherein said at least one third switch is connected to said first switch and said second switch in such a way that a closed state of said at least one third state corresponds to a simultaneous closed state of said first and second switches.

3. The apparatus of claim 1, wherein said at least one third switch is connected electrically in parallel with said first and second switches.

4. The apparatus of claim 1, wherein said at least one third switch is coupled mechanically to said first and second switches in such a way that, upon actuation of said at least one third switch, said first and second switches are simultaneously closed.

5. The apparatus of claim 1, wherein a first signal coder is assigned to said first switch and a second signal coder is assigned to said second switch, wherein said first signal coder has a first diode and said second signal coder has a second diode, said first and second diodes being connected to said control signal line with reversed polarity.

6. An electrosurgical apparatus, comprising:
   an HF generator having a first operating state, a second operating state and at least one third operating state;
   an HF instrument having a first switch assigned to said first operating state, a second switch assigned to said second operating state, and at least one third switch assigned to said at least one third operating state;
   a control signal line, said first, second and at least one third switches being connected to said HF generator via said control signal line;
   a first signal coder assigned to said first switch, a second signal coder assigned to said second switch, a third signal coder assigned to said at least one third switch is differing from said first and second signal coder;
   said first, second and at least one third switches generate a first, a second or at least one third control output signal which differ from one another, from a control input signal as a function of a switching state of said first, second and said at least one third switches, in order to optionally actuate one of said first, second and at least one third operating states of said HF generator, said first, second and at least one third control output signals being fed to said HF generator via said control signal line only.

7. The apparatus of claim 6, wherein said third signal coder assigned to said at least one third switch corresponds to a parallel connection of said first and second signal coders assigned to said first and second switches.

8. The apparatus of claim 6, wherein said third signal coder assigned to said at least one third switch has other coding properties than said first and second signal coders assigned to said first and second switches.

9. The apparatus of claim 6, wherein a first signal coder is assigned to said first switch and a second signal coder is assigned to said second switch, wherein said first signal coder has a first diode and said second signal coder has a second diode, said first and second diodes being connected to said control signal line with reversed polarity.

10. The apparatus of claim 6, wherein a signal coder is assigned to at least one of said first, second and third switches, and said signal coder has at least one Zener diode.

* * * * *